United States Patent
Cramer et al.

(10) Patent No.: US 9,188,875 B2
(45) Date of Patent: Nov. 17, 2015

(54) CALIBRATION METHOD, INSPECTION METHOD AND APPARATUS, LITHOGRAPHIC APPARATUS, AND LITHOGRAPHIC PROCESSING CELL

(75) Inventors: Hugo Augustinus Joseph Cramer, Eindhoven (NL); Maurits Van Der Schaar, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 1053 days.

(21) Appl. No.: 13/132,011

(22) PCT Filed: Dec. 1, 2009

(86) PCT No.: PCT/EP2009/066152
§ 371 (c)(1),
(2), (4) Date: Aug. 12, 2011

(87) PCT Pub. No.: WO2010/069757
PCT Pub. Date: Jun. 24, 2010

(65) Prior Publication Data
US 2011/0292365 A1 Dec. 1, 2011

Related U.S. Application Data

(60) Provisional application No. 61/122,797, filed on Dec. 16, 2008.

(51) Int. Cl.
*G03F 7/20* (2006.01)
*G01N 21/47* (2006.01)

(52) U.S. Cl.
CPC ........ *G03F 7/70633* (2013.01); *G01N 21/4785* (2013.01); *G03F 7/70516* (2013.01); *G03F 7/70616* (2013.01); *G03F 7/70625* (2013.01)

(58) Field of Classification Search
CPC ............ G03F 7/70516; G03F 7/70616; G03F 7/70625; G03F 7/70633
See application file for complete search history.

(56) References Cited

U.S. PATENT DOCUMENTS 7,710,572 B2   5/2010  Mos et al.
2003/0020912 A1*  1/2003  Norton et al. ................. 356/369
(Continued)

FOREIGN PATENT DOCUMENTS

EP   1 628 164 A2   2/2006
GB   2 257 514 A    1/1993

OTHER PUBLICATIONS

International Search Report directed to related International Application No. PCT/EP2009/066152, mailed Jun. 7, 2010, European Patent Office, Rijswijk, Netherlands; 3 pages.

(Continued)

*Primary Examiner* — Peter B Kim
*Assistant Examiner* — Michelle Iacoletti
(74) *Attorney, Agent, or Firm* — Sterne, Kessler, Goldstein & Fox P.L.L.C

(57) ABSTRACT

Disclosed are methods, apparatuses, and lithographic systems for calibrating an inspection apparatus. Radiation is projected onto a pattern in a target position of a substrate. By making a plurality of measurements of the pattern and comparing the measured first or higher diffraction orders of radiation reflected from the pattern of different measurements, a residual error indicative of the error in a scatterometer may be calculated. This error is an error in measurements of substrate parameters caused by irregularities of the scatterometer. The residual error may manifest itself as an asymmetry in the diffraction spectra.

26 Claims, 4 Drawing Sheets

(56) References Cited

U.S. PATENT DOCUMENTS

2003/0028358 A1    2/2003   Niu et al.
2004/0038455 A1    2/2004   Seligson et al.
2004/0210402 A1   10/2004   Opsal et al.
2008/0036984 A1    2/2008   Mos et al.
2008/0144036 A1*   6/2008   Schaar et al. ............... 356/446
2008/0239318 A1   10/2008   Den Boef et al.
2013/0128270 A1*   5/2013   Brill et al. ................. 356/399

OTHER PUBLICATIONS

International Preliminary Report on Patentability directed to related International Application No. PCT/EP2009/066152, mailed Jun. 21, 2011, The International Bureau of WIPO, Geneva, Switzerland; 8 pages.

* cited by examiner

CALIBRATION METHOD, INSPECTION METHOD AND APPARATUS, LITHOGRAPHIC APPARATUS, AND LITHOGRAPHIC PROCESSING CELL

CROSS-REFERENCE TO RELATED APPLICATIONS

This application claims the benefit of U.S. provisional application 61/122,797, which was filed on Dec. 16, 2008, and which is incorporated herein in its entirety by reference.

FIELD

Embodiments of the present invention relate to a method of calibrating an inspection apparatus that can be used, for example, in the manufacture of devices by lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a "mask" or a "reticle," may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (i.e., resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called "scanners," in which each target portion is irradiated by scanning the pattern through a radiation beam in a given direction (e.g., the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate such as, for example, the structure of the pattern. Knowledge of the structure of the pattern (and its accuracy) gives rise to information regarding the accuracy of the patterning system (specifically, the illumination or exposure system) that creates the pattern. The accurate formation of the pattern needs to be monitored to, for example, ensure that successive layers formed in or on the substrate are aligned to eliminate noise or cross-talk between portions of the pattern close to one another.

There are various techniques for making measurements of the microscopic structures formed in lithographic processes, including the use of scanning electron microscopes and various specialized tools. One form of specialized inspection tool is a scatterometer in which a beam of radiation is directed onto a patterned target on the surface of the substrate and the scattered or reflected beam is detected and the properties of the scattered or reflected beam are measured. By comparing the properties of the beam before and after it has been reflected or scattered by the pattern on the substrate, the properties of the pattern on the substrate can be determined. This can be done, for example, by comparing the reflected beam with data stored in a library of known measurements associated with known pattern properties.

Two main types of scatterometer are known. Spectroscopic scatterometers direct a broadband radiation beam onto the substrate and measure the spectrum (e.g., intensity as a function of wavelength) of the radiation scattered into a particular narrow angular range. Angularly-resolved scatterometers use a monochromatic radiation beam and measure the intensity of the scattered radiation as a function of angle. An extension of the use of scatterometers is the use of ellipsometers, which are systems that not only measure the intensity of the reflected light, but also measure the phase difference between different polarized states of the illuminating radiation beam that is reflected from the pattern on the surface of the substrate. Different structures (e.g., structures within the pattern) on the substrate will cause different polarized radiation to reflect (e.g., scatter/diffract) differently and properties of the structures can be determined by measuring this reflected radiation.

The scatterometer may be viewed simplistically as a system to carry out the illumination of a target and the collection of data from the reflected radiation. Such a scatterometer is often used to determine properties of the substrate or, more specifically, properties of the pattern on the substrate surface that cause the scattering/diffraction of the radiation. The properties may provide information as to the alignment of the substrate with the lithographic exposure apparatus around it. Alternatively, the properties may give information regarding the internal alignment of the substrate (namely, the alignment of its consecutively exposed layers). The properties of the pattern on the substrate may include the size, shape, and alignment of printed structures on the substrate surface or within its layers. Alignment may include overlay error (between subsequent layers). Structure parameters may include line thickness, critical dimension (CD), etc.

Sensor calibration is an essential element of known scatterometry. Sensor calibration for some known angular-resolved scatterometry systems is based upon a simplified sensor model. The simplified sensor model may be referred to as a calibration model. Imperfections in an illuminator (which provides the radiation beam for reflection and subsequent detection) and in various parts of the system that transmit signals detected by the sensor (e.g., detection of the reflected beam) are not necessarily accommodated in the model. These imperfections that are not accounted for in known sensor calibrations may be determined to be an overall calibration "residual." As sensor models generally work using the zeroth-order reflection (i.e., diffraction), the calibration residual is a residual for zeroth-order reflection. In known systems, an approximate correction has been implemented based on this zeroth-order residual. Generally, calibration models may be created based on the assumption that the illuminator and the sensor have rotational symmetry.

In order for radiation that impinges onto the substrate to diffract (in order to be measured), a pattern with a specific shape is printed on the substrate and is often known as a scatterometry target, mark, or marker. The pattern of the scatterometry target will be referred to herein as the "pattern" or the "patterned target" (e.g., when referring to the area on the substrate surface that is being measured). The pattern may include a diffraction grating and the like, which may be an array of bars or other periodic structures. The cross-section of the pattern printed on the substrate is known as the "profile" of the pattern. The profile is typically a repeating pattern such as, for example, an array of resist lines. The individual profile of each repeated portion of pattern is the individual profile of a "unit cell" of the pattern. For metrology purposes, an average is taken of a plurality of these unit cells (i.e., an average of a repeating pattern is taken) and the average of all of the individual profiles will be referred to herein as the "profile." What is commonly known as the profile of the pattern is hence a concatenation of a number of unit cells, which may contain local variations.

The profile is generally measured from the surface of the substrate and may include various product layers. Ideally, the pattern that is printed onto the substrate would have a predetermined shape and would be printed substantially identical each time it was printed on each layer (e.g., both in terms of the shape of the pattern and its relative position to the substrate). In practice, however, the shape, position and size of the pattern may deviate from the ideal shape on consecutive product layers because of the difficulty in creating accurate shapes at the small sizes of the patterns involved.

As mentioned above, it is possible to determine the actual shape of a pattern using cross-section scanning electron microscopes and the like. However, this involves a large amount of time, effort, and specialized apparatus and is less suited for measurements in a production environment because a separate specialized apparatus is required in line with normal apparatus in, for example, a lithographic cell.

Another way to determine the profile of a scatterometry pattern is to diffract a beam of radiation from the pattern and compare the diffraction pattern with model diffraction patterns that are stored in a library of diffraction patterns alongside the model profiles that create these model patterns.

U.S. Pub. Pat. Appl. No. 2003/0028358 to Niu et al. (hereinafter "Niu"), which is incorporate herein by reference in its entirety, describes a system in which an actual signal from a pattern is compared with a library of stored signals and the system finds a closest match of signals. The stored signals are each linked to a set of pattern profile parameters. A pattern profile parameter may, for instance, be the critical dimension (CD) or width of the pattern (which may vary with height), the height of the pattern or the angle of a side surface (or "sidewall") of the pattern. This sidewall angle may be measured either from the surface of the substrate or from a normal to the substrate surface. Niu also describes a method to find a closest match between the measured signal and a calculated signal of a model of the scatterometry pattern, where the shape of the model depends on the values of the profile parameters in the model. In other words, various possible sets of parameter values are tested to find a set that gives rise to a signal that is as close to the actual signal that has come from the scatterometry pattern as possible. This gives a series of iterations of a "model signal." This method is repeated iteratively until the model signal is as close as possible to the actual signal and then the model signal is stored alongside the parameters used.

In another document, U.S. Pub. Pat. Appl. No. 2004/0210402 to Opsal et al. (hereinafter "Opsal"), which is incorporated by reference herein in its entirety, defines a system that aims to reduce the number of parameters required to build up the profile of a pattern from the scatterometry signals. In doing so, the system provides "control points" around the outside of the profile shape from which the profile shape may be built up. For example, a square-profiled pattern has a single control point to show its height from the substrate surface and two points to show a width. The points are then joined up in a "dot-to-dot" fashion to give a line profile.

The systems described above only find a single profile. Further, calculations provided by the systems are required to find a "profile space" (i.e., a combination of a generic profile description with a number of profile parameters) and the possible ranges of those parameters. This combination builds up a specific profile space as required. For example, a user may choose to describe a profile by a trapezoid with parameters of width, height, and sidewall angle. The user then defines ranges for these three parameters. More complex profiles are built in a similar fashion, for example, with more complex shapes or a series of trapezoids amalgamated together.

The system described above uses a library of model profiles in order to find the best match. Other systems either do not use libraries or are used in combination with libraries. An alternative system (also described above) is an iterative method, where the parameters are given a starting value and the diffraction pattern of these starting values is calculated and compared with the measured diffraction pattern. The values of the parameters are then iteratively changed to improve the match between the iteratively modeled and the measured diffraction pattern. This iterative method may be combined with the library method.

The methods and systems described above, however, cannot be used to its full potential if there are errors in the scatterometer (particularly, if the errors in the scatterometer vary from measurement to measurement). An error may occur in the scatterometer that is used to measure the profile of the pattern. An error may also occur at any time during the scatterometry process. An error may occur during the printing of the pattern on the substrate such that there is an error in the pattern. Alternatively (or additionally), the illumination system may contain an error such that radiation that is transmitted to the patterned area of the substrate may be incorrectly aligned or have a slight error in wavelength, intensity, etc. Yet alternatively, an error may occur in the sensing of the reflected radiation, either in the optical apparatus that directs reflected radiation to the sensor, or in the sensor itself. With respect to the sensor, an anomaly may occur with the sensor itself. Dust or scratches will affect the intensity of the illumination that is detected. The impact of these anomalies may vary as a function of the angle and/or wavelength of the radiated or the reflected beam.

A scatterometer that "uses" diffraction as its metrology tool will transmit a radiation beam onto the patterned target and measure, using a sensor, the beam that is diffracted. Changing the angle and/or wavelength at which the radiation beam impinges on the pattern will cause a change in the resultant diffraction pattern. The magnitude of the change in the diffraction pattern is dependent on the properties of the pattern on the substrate. One component of the variation in the diffraction pattern is known as an "asymmetry" because there can be a difference (in intensity) between the "+1" and the "−1" diffraction orders even though both orders are a result of diffraction of the same radiation beam from the same portion of the pattern. The same can be true for higher diffraction orders. The variation arises when there is an error somewhere in the scatterometry system. The type of asymmetry detected can give clues as to where in the scatterometry system an error exists.

A scatterometer must be able to take these sorts of inconsistencies into account if it is to measure correctly the profile of a pattern.

Currently, an inspection apparatus such as an angular-resolved scatterometer is calibrated using a simplified sensor model that does not take into account all of the causes of the error. The sensor model may be calibrated using measurements on known unpatterned targets (e.g., based on zeroth-order diffraction).

In critical dimension (CD) scatterometry, one of the important performance parameters is a tool-induced error. Tool-induced error factors include rotational asymmetries in the illumination system and in sensor information transmission. The zeroth-order residual correction does not work correctly, for example, in a case of a diffraction grating as a pattern on the substrate that has a higher diffraction order.

SUMMARY

It is desirable to calibrate an inspection apparatus. Current calibration methods use a sensor model that incorporates properties of the inspection apparatus that may likely cause errors in the exposure of a pattern on the substrate. It is further desirable that calibration methods more accurately account for the induced error caused by the scatterometer (or more generally, the inspection apparatus) itself as compared to other calibration methods.

The impact of illumination and sensor transmission asymmetry on a measured pupil plane depends on the properties of the patterned target from which reflected radiation is measured—in particular, on the presence and location of first or higher diffraction orders in the pupil plane. It is desirable to determine the amount of residual error that remains after a generic calibration and to take it into account when exposing a pattern on a substrate.

According to an embodiment of the present invention, a method of calibrating an inspection apparatus to account for an error in said inspection apparatus (that is not accounted for in the sensor model) is provided. The method includes the following: making at least two measurements of a patterned target on a substrate, wherein at least one of said at least two measurements is made using said inspection apparatus and each measurement comprises: projecting a beam of radiation onto said patterned target; measuring at least one diffraction order of radiation reflected from said patterned target (optionally correcting the measurements using embodiments of the calibration method); and, calculating a residual error indicative of the error of said inspection apparatus, wherein the residual error is a variation in intensity of at least one diffraction order of radiation reflected from said target caused by the error in the inspection apparatus (not incorporated in the calibrated sensor model), wherein said calculating of the residual error includes comparing said at least two measurements (optionally after correcting the measured orders using embodiments of the calibration method).

According to a further embodiment of the present invention, a method of measuring the critical dimension of a pattern in a patterned target on a substrate using an inspection apparatus, accounting for an error in said inspection apparatus (or a deviation of the inspection apparatus from the calibrated sensor method), where the error causes an error in a measurement of at least one diffraction order of radiation reflected from said patterned target is provided. The method includes the following: making at least two preliminary measurements of diffraction spectra of radiation diffracted from the patterned target on the substrate using said inspection apparatus, wherein a comparison of said at least two preliminary measurements is indicative of the error in said inspection apparatus and gives rise to a residual error in the diffraction spectra, each preliminary measurement comprising: projecting a beam of radiation onto said patterned target; measuring at least one diffraction order of radiation reflected from said patterned target, wherein the orientation of said patterned target with respect to said inspection apparatus for at least one of said at least two preliminary measurements is rotated by an angle θ about a normal to the plane of the substrate compared to the orientation of said patterned target for another at least one of said at least two preliminary measurements; using said residual error to correct a preliminary measurement of the diffraction spectra diffracted from the patterned target; and, using said corrected preliminary measurement of the diffraction spectra diffracted from the target to determine the critical dimension of the pattern in the patterned target.

According to yet another embodiment of the present invention, an inspection apparatus configured to measure a parameter of a substrate is provided. The apparatus includes the following: a radiation projector configured to project radiation onto a patterned target on said substrate; a detector configured to detect the radiation reflected from the patterned target, wherein said reflected radiation includes a diffraction spectrum with at least one diffraction order; a calibration unit configured to calculate a residual error, wherein the residual error is the error in measurement of the diffraction spectrum diffracted from the substrate caused by an error in the inspection apparatus (or a deviation of the inspection apparatus from a sensor model); and, a data handling unit configured to calculate the parameter on the basis of said reflected radiation reflected from said patterned target and said residual error, wherein calculating said residual error comprises: making at least two measurements of a calibration target on a substrate, wherein at least one of said at least two measurements is made using said inspection apparatus and each measurement comprises: projecting a beam of radiation onto said calibration target; and measuring at least one diffraction order of radiation reflected from said calibration target; and calculating the residual error by comparing the at least two measurements.

Embodiments of the present invention are also directed to a lithographic apparatus and a lithographic cell containing features of the inspection apparatus as defined above.

Further features and advantages of present invention, as well as the structure and operation of various embodiments of the invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

The features and advantages of embodiments of the present invention will become more apparent from the detailed

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include the following: read only memory (ROM); random access memory (RAM); magnetic disk storage media; optical storage media; and, flash memory devices. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
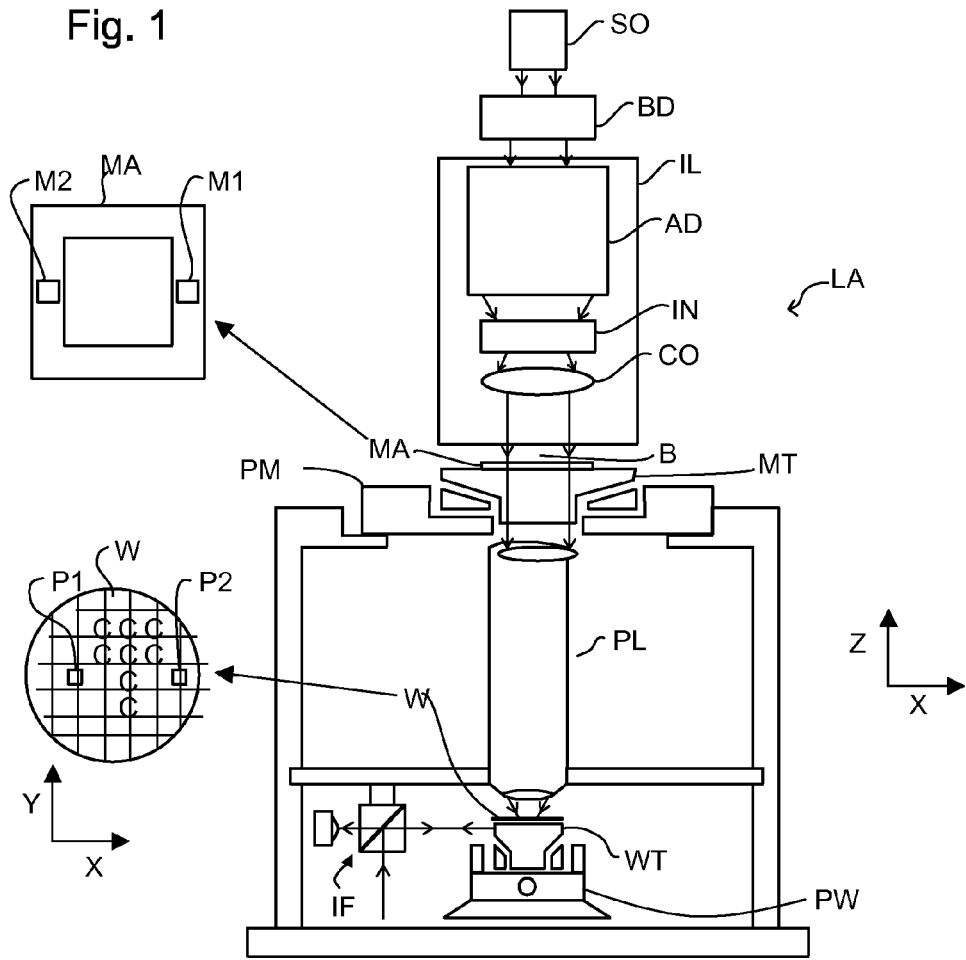
FIG. 1 is an illustration of an example lithographic apparatus, in which embodiments of the present invention may be implemented.

FIG. 1 schematically depicts a lithographic apparatus LA. The apparatus comprises:

an illumination system (illuminator) IL configured to condition a radiation beam B (e.g., UV radiation or DUV radiation).

a support structure (e.g., a mask table) MT constructed to support a patterning device (e.g., a mask) MA and connected to a first positioner PM configured to accurately position the patterning device in accordance with certain parameters;

a substrate table (e.g., a wafer table) WT constructed to hold a substrate (e.g., a resist-coated wafer) W and connected to a second positioner PW configured to accurately position the substrate in accordance with certain parameters; and, a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as, for example, refractive, reflective, magnetic, electromagnetic, electrostatic or other types of optical components, or any combination thereof, for directing, shaping, or controlling radiation.

The support structure supports (i.e., bears the weight of) the patterning device. It holds the patterning device in a manner that depends on the orientation of the patterning device, the design of the lithographic apparatus, and other conditions such as, for example, whether or not the patterning device is held in a vacuum environment. The support structure can use mechanical, vacuum, electrostatic, or other clamping techniques to hold the patterning device. The support structure may be a frame or a table, which, for example, may be fixed or movable as required. The support structure may ensure that the patterning device is at a desired position with respect to, for example, the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so-called "assist" features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index (e.g., water) so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example, when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example, when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as "σ-outer" and "σ-inner," respectively) of the intensity distribution in a pupil plane of the illuminator can be adjusted. In addition, the illuminator IL may include various other components, such as an integrator IN and a condenser CO. The illuminator may be used to condition the radiation beam to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder, or capacitive sensor), the substrate table WT can be moved accurately (e.g., so as to position different target portions C in the path of the radiation beam B). Similarly, the first positioner PM and another position sensor (which is not explicitly depicted in FIG. 1) can be used to accurately position the mask MA with respect to the path of the radiation beam B (e.g., after mechanical retrieval from a mask library or during a scan). In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as "scribe-lane alignment marks"). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the x and/or y-direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-) magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above. Combinations and/or variations on the above described modes of use or entirely different modes of use may also be employed.

Figure 2:
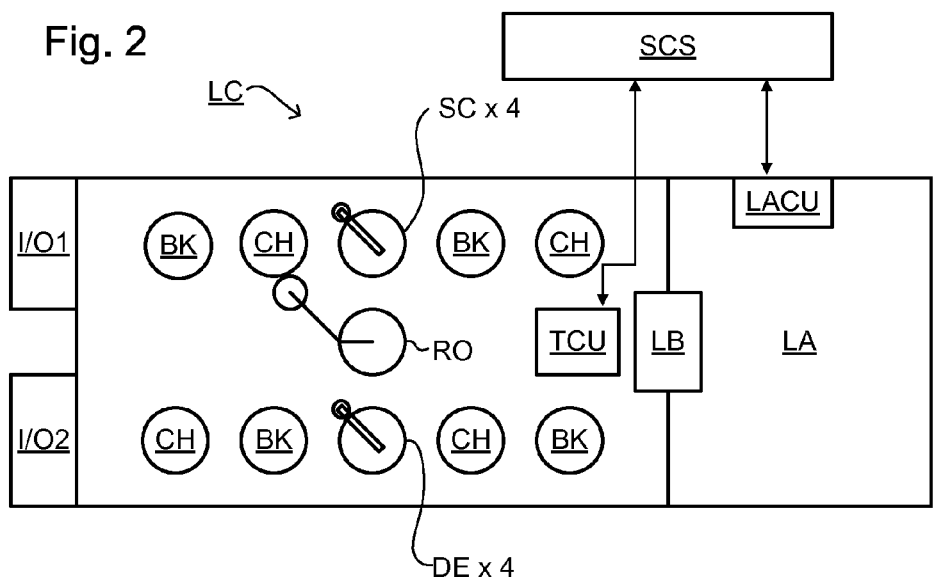
FIG. 2 is an illustration of an example lithographic cell or cluster, in which embodiments of the present invention may be implemented.

As shown in FIG. 2, the lithographic apparatus LA forms part of a lithographic cell LC, also sometimes referred to as a "lithocell" or "cluster," which also includes apparatus to perform pre- and post-exposure processes on a substrate. Conventionally, these include spin coaters SC to deposit resist layers, developers DE to develop exposed resist, chill plates CH, and bake plates BK. A substrate handler, or robot, RO picks up substrates from input/output ports I/O1, I/O2, moves them between the different process apparatus, and delivers them to the loading bay LB of the lithographic apparatus. These devices, which are often collectively referred to as the "track," are under the control of a track control unit TCU which is itself controlled by the supervisory control system SCS, which also controls the lithographic apparatus via a lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough such that other substrates of the same batch that still need to be exposed can take advantage of the adjustments. Also, already-exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist that have been exposed to radiation and those which have not—and not all inspection apparatus have sufficient sensitivity to make useful measurements of the latent image. Therefore, measurements may be taken after the post-exposure bake step (PEB), which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
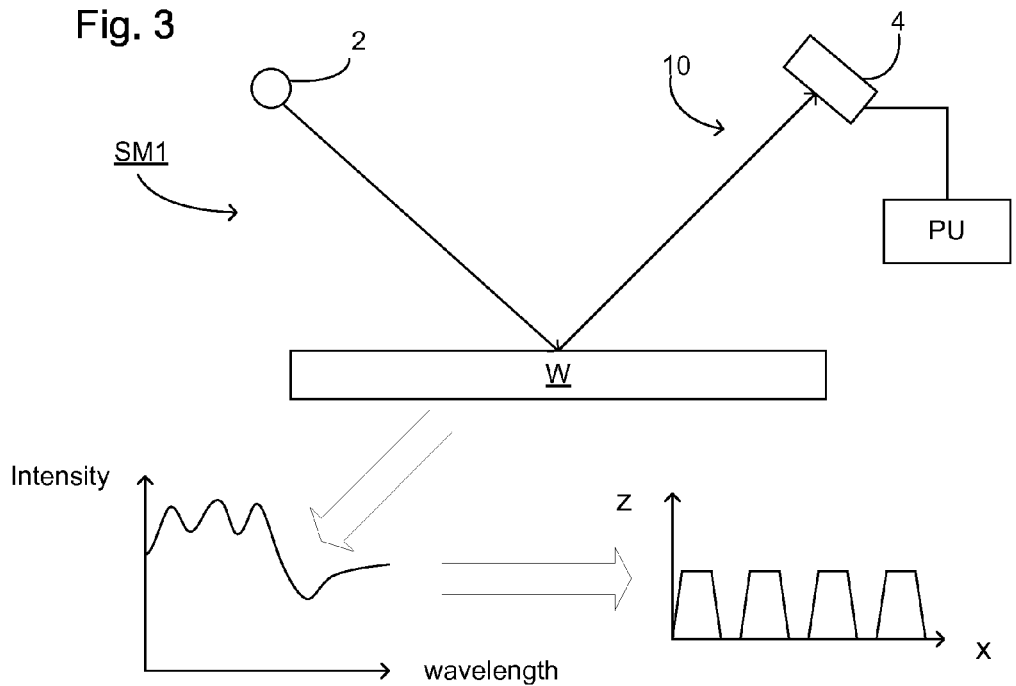
FIG. 3 is an illustration of an example scatterometer, in which embodiments of the present invention may be implemented.

FIG. 3 depicts an inspection apparatus in the form of a scatterometer SM1, which may be used in embodiments of the present invention. Scatterometer SM1 includes a broadband (white light) radiation projector 2, which projects radiation onto a substrate W. The reflected radiation is passed to a spectrometer detector 4, which measures a spectrum 10 (e.g., intensity as a function of wavelength) of the specular reflected radiation. From this data, the structure or profile giving rise to the detected spectrum may be reconstructed by processing unit PU (e.g., by Rigorous Coupled Wave Analysis and non-linear regression or by comparison with a library of simulated spectra as shown at the bottom of FIG. 3). In general, for the reconstruction, the general form of the structure is known and some parameters are assumed from knowledge of the process by which the structure was made, leaving a few parameters of the structure to be determined from the scatterometry data. Such a scatterometer may be configured as a normal-incidence scatterometer or an oblique-incidence scatterometer.

Figure 4:
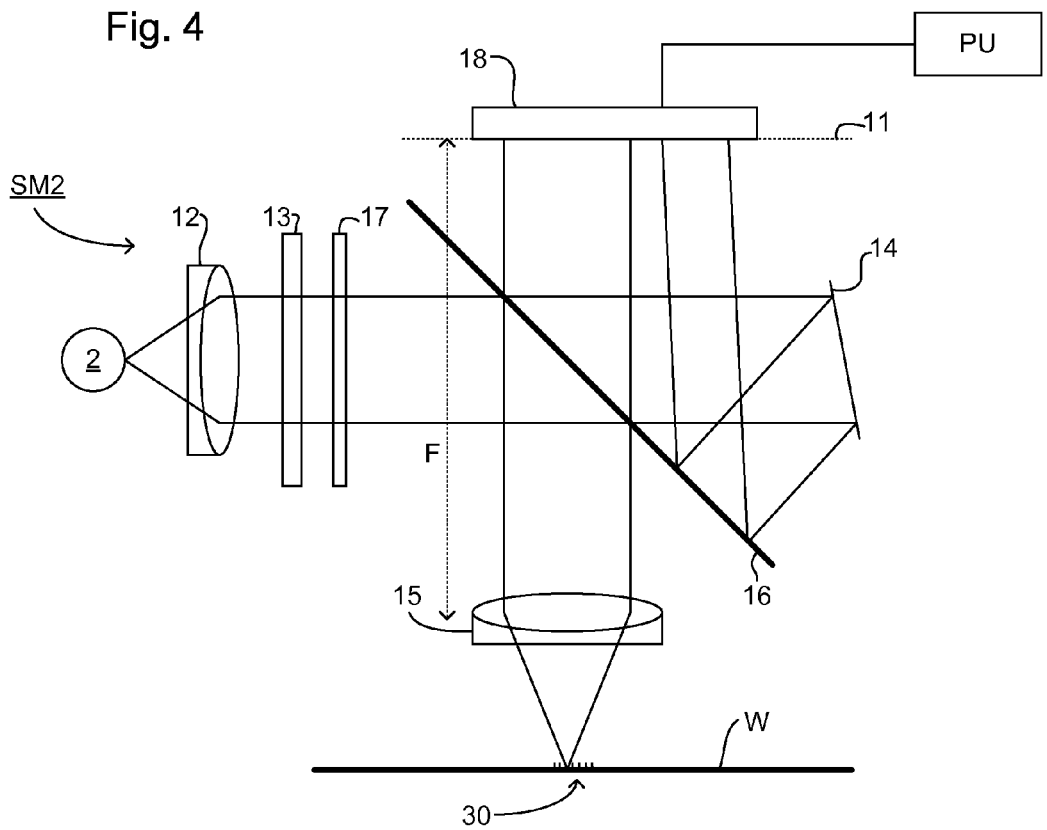
FIG. 4 is an illustration of another example scatterometer, in which embodiments of the present invention may be implemented.

Another scatterometer SM2 that may be used with embodiments of the present invention is shown in FIG. 4. In this device, the radiation emitted by radiation source 2 is focused using lens system 12 through interference filter 13 and polarizer 17, reflected by partially reflective surface 16 and is focused onto substrate W via a microscope objective lens 15, which has a high numerical aperture (NA) (e.g., at least 0.9 or at least 0.95). Immersion scatterometers may even have lenses with numerical apertures over 1. The reflected radiation then transmits through partially reflective surface 16 into a detector 18 in order to have the scattered spectrum detected. The detector may be located in the back-projected pupil plane 11, which is at the focal length of the objective lens 15; however, the pupil plane may instead be re-imaged with auxiliary optics (not shown) onto the detector. The pupil plane is the plane in which the radial position of radiation defines the angle of incidence and the angular position defines azimuth angle of the radiation. In one example, the detector is a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used, for example, to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, for example, 405-790 nm or a lower range, such as, for example, 200-300 nm. The interference filter may be tunable rather than including a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths) is possible, which gives a large etendue, allowing the mixing of multiple wavelengths. The plurality of wavelengths in the broadband each has a bandwidth of $\Box\Box$ (i.e., a small proportion ($\Box$) of the wavelength ($\Box$) such as, for example, on the order of 10 nm) and a spacing of at least 2$\Box\Box$ (i.e., twice the bandwidth). Several "sources" of radiation can be different portions of an extended radiation source that have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

Figure 6:
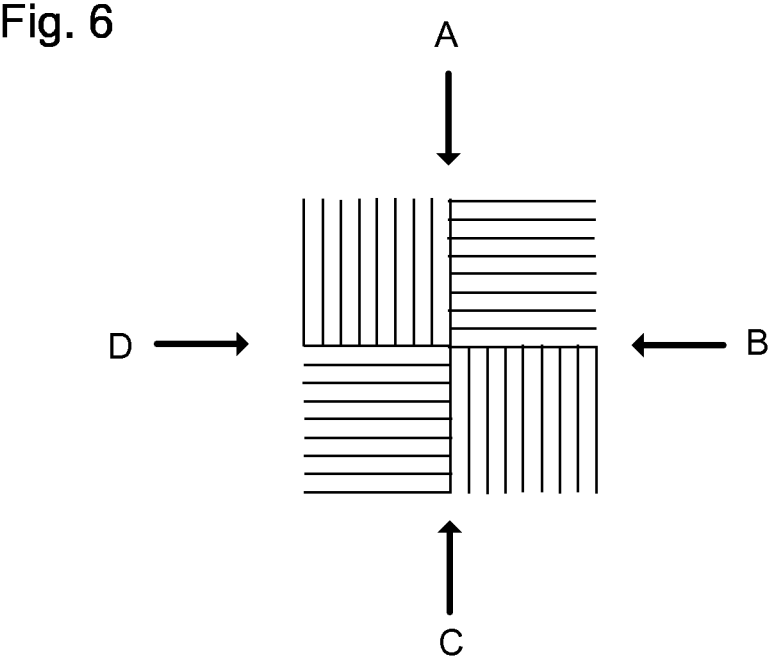
FIG. 6 is an illustration of an example of a grating-based patterned target, in which embodiments of the present invention may be implemented.

The pattern 30 on the target portion of the substrate W may be a grating (for example, one or more of the quarters as shown in FIG. 6), which is printed such that after development, the bars are formed of solid resist lines. The bars may alternatively be etched into the substrate W. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU from knowledge of the printing step and/or other scatterometry processes.

Most current metrology applications (e.g., profile measurement) require one or more dedicated targets (such as one or more overlay targets) because only then is it possible to obtain "direct" performance metrics such as overlay and CD/sidewall-angle absolute measurements. Some metrology applications do not aim at direct performance measurements and may therefore also be used for in-die measurements. By "direct performance measurements," it is understood that the measurement is carried out on a dedicated test structure, such as a diffraction grating. On the other hand, "in-die" measurements can be carried out on a product layer of the substrate as an intermediate or final product. In-die measurements save time and substrate surface space over direct performance measurements by not requiring one or more special test structures to be formed and being able to be carried out effectively "on the fly."

As an alternative to using an existing printed product pattern, the structure or pattern that is measured may be a dedicated target such as a diffraction grating (e.g., with a specific period and phase). If a dedicated target is used, it is easier to meet the criterion of having a repeating structure, which makes it much easier to notice a variation in, for example, the phase of the repeating structure that could indicate a fault. The positional invariance of the back focal plane that is useful to an embodiment of the present invention also relies to some extent on having a repeating structure.

Imperfections in the scatterometer used for measuring the properties discussed above may lead to unwanted irregularities in the pattern printed on the substrate. Imperfections in the scatterometer will first appear as errors (also known as "offsets") in the detected data. Corrections are made to this "raw" detected data to give calibration data. The calibration data may give rise to a "calibration model" as mentioned above. To calibrate measured data, the calibrated data is subtracted, added, multiplied, or divided by the measured data. The calibration and measured data may be in the form of images or spectral functions. Once calibrated, diffraction spectra may be used to determine the properties of the pattern on the substrate surface without the errors caused by scatterometer imperfections. However, after calibration, there may remain some errors that are not caught by the calibrated data. What remains (usually in the first and higher diffraction orders) is a "residual error." One example of how a residual error manifests itself in a diffraction spectrum image is as an asymmetry between "+1" and "−1" diffraction orders, for instance (or higher diffraction orders). Hence, in this particular type of measurement, an error in the inspection apparatus (that gives rise to an asymmetry in a diffraction spectrum) may be referred to as an "asymmetry error" (or an asymmetry offset).

In an embodiment of the present invention, raw data that is collected in the back focal plane (also known as the back-projected pupil plane or the Fourier plane) of a scatterometry-based sensor is used. This is simply the intensity image of, for example, a CCD sensor 4 as shown in FIG. 3. The monitoring for a fault can be done by monitoring a change of this image acquired with a structure pattern that is expected not to vary. The raw data that is collected is an intensity image of the diffracted radiation, without further manipulation that takes unnecessary time as discussed above. The intensity image is compared with existing data in order to determine what differences there are in the intensity image with respect to the expected intensity image. A difference between the images indicates a processing error (such as an overlay error or an imaging error).

The difference in the images is often recognized by superimposing the two images on top of each other, or subtracting one from the other. Variations in intensity are often visible even to the naked eye in the compared images.

Because this intensity image can also be used to calculate parameters such as, for example, critical dimension, side-wall angle, and so on, data showing the variation of one or more of these metrics is also present in the CCD image of the sensor 4. It is with the variation in one or more of these measurements that an embodiment of the present invention is able to determine a process excursion or fault. Specifically, a library (as described above) or database of the raw data for one or more known pattern shapes and errors in the shapes is created and added to as various exposure tests are carried out. The raw image data can therefore be directly compared with known data and the fault that gives rise to the variation in the raw image data can be determined. In summary, the intensity distribution of the back focal plane image is a function of one or more performance measures. As such, a variation in the intensity distribution of the back focal plane image is an indication of a change in that performance measure(s).

When measuring the properties of substrates with first-order diffraction angles, the residual error after calibration can typically be in the 1 nm range, which may not meet the required accuracy standard. Additionally, there is the problem that scatterometers cannot be matched to each other sufficiently such that accurate measurements are consistent across different scatterometers.

Imperfections in the scatterometer lead to unwanted errors in the patterning process of the substrate W, such as overlay errors between subsequent layers, line thickness errors, critical dimension (CD) errors, and other profile parameter irregularities.

Typically, the scatterometer is calibrated in an attempt to account for these imperfections. However, current calibration models are based on the assumption that the illumination and transmission of the scatterometer are rotationally symmetric (e.g., homogeneous). Only zeroth-order reflections from the substrate W are used to calibrate the model; in other words, only the zeroth diffraction order is used to determine the correction in measured diffraction spectra used to calculate the parameter values of the substrate W. Therefore, the calibration does not take into account all aspects of the scatterometer (only those measurable in the zeroth order).

Deviations in the scatterometer from the calibrated sensor model undesirably affect the measurement of parameters that rely on the detection of reflected radiation from the substrate W. This is because, as described above, different components of the diffraction spectrum may be used to determine the profile parameters (such as critical dimension (CD)) of the target pattern. Additional disturbances (from irregularities in the illumination beam or sensor) of the diffracted beam may be incorporated into the calculations of profile error and may lead to miscalculations of the profile. Deviations from the calibrated sensor model caused by irregularities in the illumination beam or sensor (i.e., the transmission beam) that are not covered in the calibrated sensor model must therefore be accounted for.

As an example, overlay error is calculated from the difference in intensities of first-order radiation reflected from a substrate W. An error such as an asymmetry in the scatterometer used for making the overlay error measurement leads to false values of the difference in intensities of first-order radiation reflected from the substrate W. This results in errors in the overlay measurements. Alternatively, the measurement of the profile of a pattern (such as a grating) will have errors if an asymmetry is measured (in the diffraction spectrum) that is attributable to the illumination beam (or the sensor) and not to the grating itself. Current calibrations use a sensor model that does not incorporate all possible sources of error in the scatterometer itself.

Therefore, it is desirable to extend the calibration of the scatterometer to account for the residual error (i.e., error not compensated for by comparison with a model) caused by scatterometer error. In an embodiment of the present invention, where the following is possible, the source of the error in the scatterometer may be determined and this error may be translated into a variation in the diffraction spectrum of reflected radiation. The variation may then be used to correct the diffraction spectrum and thereby correct any measurements of the patterned substrate ("tool calibration"). Alternatively, the calibration may include determining the difference in detected radiation (e.g., asymmetry in diffraction orders) between the scatterometer and a reference scatterometer ("tool-to-tool" or "tool-to-golden tool" calibration, where the golden tool is the reference scatterometer).

The error induced by the asymmetry of a scatterometer into the measurements of the substrate's properties is known as the asymmetry error or asymmetry offset (AO). Dominant contributors to the asymmetry of the scatterometer include the illumination asymmetry (from the radiation beam or its source) and the transmission asymmetry (from the path the radiation beam takes such as, for example, after diffraction). The transmission asymmetry is the asymmetry of the lens system 15 (and partially reflective surface 16). It may be unfeasible to produce a perfectly rotationally symmetric lens system 15. For example, any dust particle and/or scratch on any lens of the lens system 15 causes asymmetry. The illumination asymmetry effect is the combined effect due to any asymmetry in components of the scatterometer in the optical path of the reference beam, such as radiation source 2, lens system 12, interference filter 13, and polarizer 17 (and partially reflective surface 16). For example, the radiation emitted from the source 2 may not be perfectly homogeneous, or a lens may not be perfectly homogeneous.

The effect of the illumination asymmetry may be monitored using the reference beam mentioned above. The reference beam may, for example, not reflect off the substrate W or pass through the lens system 15 and is therefore less affected by the transmission asymmetry. The transmission asymmetry effect may be measured indirectly by measuring the total asymmetry error (AO) and subtracting the measured illumination asymmetry effect (Transmission Asymmetry effect=Asymmetry error−Illumination Asymmetry effect).

Some residual transmission asymmetry may remain from the reflection of the radiation beam from either the reflective mirror 16 or the reference mirror 14. This may also be accounted for by their removal during various calibration exercises.

Generally, the transmission asymmetry effect depends on the pitch of the pattern grating, the wavelength of the illuminating radiation, and polarization of the illuminating radiation. Therefore, it is desirable to determine the transmission asymmetry effect for all combinations of these factors. In that way, measured patterning error values can be corrected according to each of these factors.

The scatterometer calibration does not need to be performed for every parameter measurement or substrate W individually. For example, in an embodiment, the calibration may be performed once for each batch of substrates. However, the frequency of calibration may be shorter or longer than this, depending on how frequently variations or errors are likely to occur or, more specifically, on how quickly variations are likely to change. A correction only works for as long as the error remains constant. If the error changes, the correction for it also changes.

The scatterometer is calibrated to account for the asymmetry error in the scatterometer. At least two measurements of the pattern 30 on a substrate W are made. At least one of the measurements is made using the scatterometer that is to be calibrated.

Figure 7:
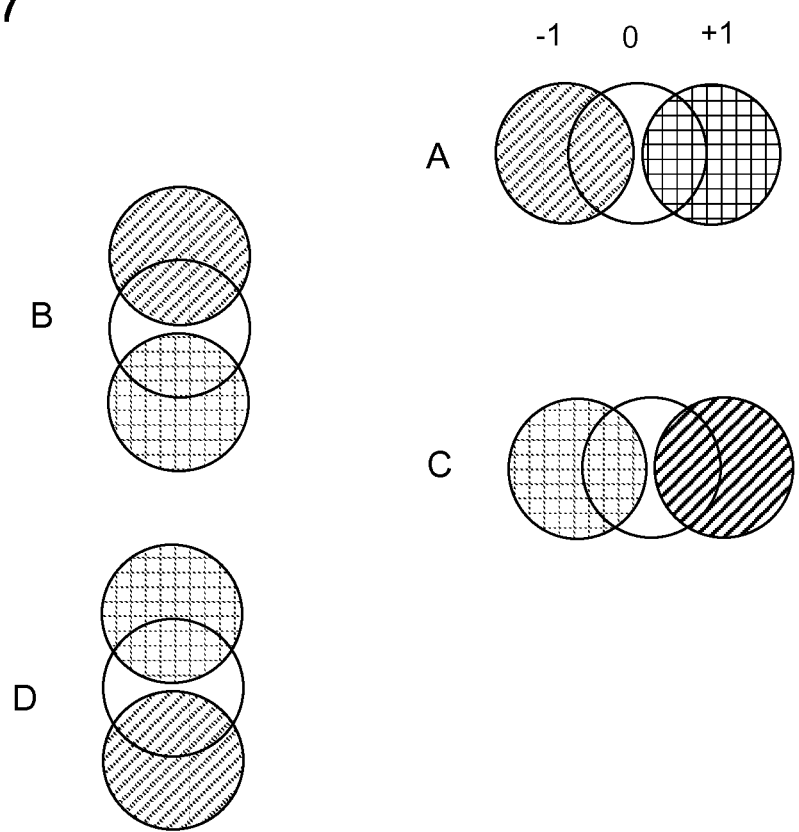
FIG. 7 is an illustration of an example of diffraction spectra result at four different diffraction angles.

In order to make a measurement, a radiation beam is projected onto the pattern 30 on the substrate W. The radiation beam may be linearly polarized. The pattern 30 may include a single grating such as a single quarter of the grating shown in FIG. 6, or a plurality of gratings, such as the entirety of the grating shown in FIG. 6. The first and/or higher diffraction orders of radiation reflected from the pattern 30 are measured. The result of the measurement is a diffraction pattern on the sensor 18. An illustrative example of a diffraction pattern as might be detected on the sensor 18 is shown in FIG. 7. FIG. 7A shows, for example, a diffraction spectrum that contains the zeroth order as a middle circle. Zeroth order is the detected intensity of the illumination that is present in the detector when the radiation beam is diffracted from an angle that is normal to the surface of the pattern 30 on the substrate W. FIG. 7A also shows two circles on either side of the zeroth order which are labeled "−1" and "+1," which are the positive and negative first diffraction orders. The first and higher diffraction orders appear when the incident radiation beam on the pattern 30 is at an angle (in fact, the positive and negative orders are created from the incident beam illuminating the pattern first from one angle and then from the opposite angle). Higher diffraction orders represent an incident angle that is further from the normal. For this reason, because a detector only has a limited numerical aperture on the receiving lens, higher diffraction orders may be difficult to detect.

A residual error (in the diffraction spectrum) is indicative of the error in the scatterometer that is not incorporated in the calibrated sensor model. The residual error may be calculated by comparing the first or higher diffraction orders of radiation reflected from the pattern 30 of at least two of the measurements made. Although diffraction orders other than the first order may be used, the first diffraction order is the easiest to measure (as detection of higher diffraction orders depends on the numerical aperture of the lens system associated with the detector, and a lower numerical aperture and therefore lower diffraction order is easier to arrange). Therefore, in an embodiment of the present invention, the first order diffraction of measured radiation from the measurements is compared.

A First Embodiment of the Present Invention

According to a first embodiment of the present invention, the asymmetry error is calculated by making multiple measurements of a pattern 30 using the same scatterometer. A comparison of the first or higher diffraction order radiation reflected from the pattern 30 can be used to calculate the error induced by the asymmetry of the scatterometer and thereby a calibration value known as the residual error.

In following the above-described procedure, a first measurement of the pattern 30 on the substrate W is obtained. The orientation of the pattern 30 with respect to the scatterometer is then changed. Rotating the substrate W (e.g., by rotating the substrate table WT holding the substrate W), the scatterometer SM2 or both the substrate W and the scatterometer SM2 change the orientation of the pattern with respect to the scatterometer. Alternatively, to change the angle of incidence of the incident beam, the substrate may be tilted. The rotation is performed about the main optical axis of the scatterometer. The main optical axis of the scatterometer passes through the center of the lens system 15.

After rotation, the pattern 30 has a different orientation with respect to the scatterometer from the orientation used during the first measurement. This is shown in a combination of FIGS. 6 and 7. FIG. 6 shows an example of the pattern that might be used by the scatterometer in order to determine whether the scatterometer has any asymmetry error. Labels A, B, C, and D in the figures give examples of angles from which the incident illumination beam may be sourced. FIG. 7 shows examples of how the first order diffraction angles might appear at each of the angles of incidence of the radiation beam. The angle of relative rotation □ may be any value. For instance, FIGS. 6 and 7 show the following angles: angle A to be 0°, B to be at 90° with respect to direction A; direction C to be 180° with respect to direction A; and, direction D as being 270° with respect to direction A. It is possible simply to use measurements in directions A and C (e.g., 0° and 180°), though the four directions A, B, C, and D in order to give a more accurate measurement. Small values of □ may also be used that are less than 90°. However, very small values of □ that are close to 0° cause the calculation of the asymmetry error to be more susceptible to noise. Once the rotation of the pattern 30 with respect to the scatterometer has been made, a second measurement of the pattern 30 is made.

In an embodiment, at least two measurements are made at different rotation orientations for determining the asymmetry error. The accuracy of the asymmetry error determination may be improved by acquiring more measurements of the pattern 30 at more orientations of the pattern 30 with respect to the scatterometer SM2. In one embodiment, at least three measurements of the pattern 30 are made at three different rotation orientations.

In order to further reduce the effect of noise (besides not using very small values of ☐), the measurements made at each substrate orientation may be repeated multiple times and an averaged value for each orientation may be calculated.

The asymmetry error is calculated from the two measurements. The first or higher diffraction order patterns in the sensor images resulting from the measurements are compared to each other. The sensor images resulting from the measurements at different substrate orientations correspondingly have different orientations. In an embodiment, the sensor image of one measurement is rotated to match the orientation of the sensor image from another measurement in order to facilitate the comparison. The reason for the rotation may be shown by the illustration in FIG. 7. For example, the diffraction spectrum shown for direction B in FIG. 7B is shown to be rotated by 90° with respect to the diffraction spectrum of direction A. By rotating the diffraction spectrum of direction B so that it is in the same orientation as the diffraction spectrum for direction A, the two diffraction spectra may be superimposed and subtracted from each other. When the intensity of B, for example, is subtracted from the intensity value of diffraction spectrum of direction A, the difference in intensity is the asymmetry error. The same applies for the diffraction spectrum of direction C, which is rotated with respect to the direction A by 180°. The same is again true for direction D, which is rotated by 270°. Rotating each of these diffraction spectra respectively and superimposing them onto, for example, the diffraction spectrum of direction A will manifest an asymmetry in the first diffraction order, from which a residual error can be determined. The inhomogeneity of the illumination or transmission beam may therefore be calculated based on the difference (i.e., the asymmetry) in the diffraction spectrum in each of the different directions.

In an embodiment, the pitch of the pattern 30, the polarization of illuminating radiation (ellipsometry), and the wavelength of the illuminating radiation (spectroscopic scatterometry) are varied and the asymmetry error measured again. These factors may be varied independently of the others. For example, the wavelength of radiation may be varied without varying the pitch or polarization. Once the asymmetry error has been determined over suitable ranges of one or more of these factors, subsequent measurements made using the scatterometer may be corrected to take into account the asymmetry error.

Figure 5:
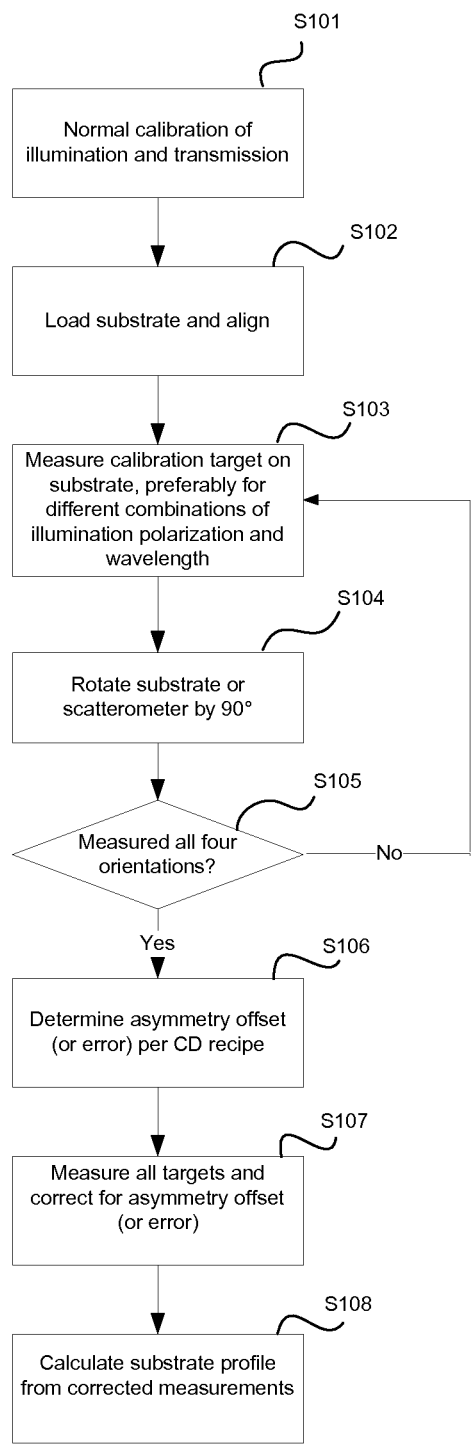
FIG. 5 is an illustration of a flow diagram of a calibration process according to an embodiment of the present invention.

As mentioned above, in one embodiment, four rotation angles are used, namely 0°, 90°, 180° and 270°. FIG. 5 illustrates a calibration process where these four rotation orientations are used. At step S101, the scatterometer is calibrated using the standard calibration model (e.g., using the zeroth diffraction order, as described in U.S. patent application Ser. No. 11/500,494, filed Aug. 8, 2006), which does not take into account the asymmetry of the scatterometer. This means that there will be a residual error induced by the deviations of the scatterometer itself from the calibrated sensor model (and not necessarily by irregularities in the pattern, which are the object of the investigation by the scatterometer).

At step S102, a substrate W is loaded onto the substrate table WT of a lithographic apparatus. The substrate W is then aligned (e.g., with respect to an alignment sensor, model, or other known alignment system).

At step S103, a pattern 30 on the substrate W is chosen as the pattern to be used for the calibration process and may look like the pattern of FIG. 6. This pattern 30 may be termed the calibration pattern 30. The calibration pattern 30 is measured. At this point, the polarization and/or wavelength of the illumination may be varied and the pattern 30 measured again. In this way, the variation in asymmetry error depending on the polarization and/or wavelength of the illumination can be monitored. In an embodiment, multiple measurements are made at each orientation with the same polarization and wavelength and an averaged value is calculated.

At step S104, the substrate W is rotated relative to the scatterometer by 90°, although other angles are also possible, as mentioned above.

At step S105, a determination is made whether or not the calibration pattern 30 has been measured for all four orientations. If it has, the process continues to step S106. If it has not, the process returns to step S103 and the calibration pattern 30 is measured at the new orientation.

At step S106, the residual asymmetry error (or residual error or calibration value) is determined by comparing the measurements made at the different orientations.

At step S107, all desired patterns (of which there may be a large number to ensure that the substrate is being exposed correctly all over its surface) on the substrate W are measured. The measurements are corrected using the residual asymmetry error (calibration value) determined in step S106.

At step S108, a profile of the (pattern on the) substrate W is calculated based on the corrected raw measurements (i.e., diffraction spectra) of all patterns on the substrate W.

An example of calculating the asymmetry error in a scatterometer from two measurements of a pattern 30 will be explained with reference to overlay error measurements for exemplary purposes only. This expands the overlay measurement method of U.S. patent application Ser. No. 11/606,376, which is incorporated herein by reference in its entirety. The same sort of calculation of profile, CD metrology, etc., may also be made using the calibration value as described above.

The above-described method of calibrating a scatterometer to account for the asymmetry error by using the scatterometer to make measurements of a pattern 30 at multiple orientations and comparing the first or higher diffraction order of measured radiation from the measurements is not restricted to overlay error measurements. The method is equally applicable to other forms of measurement that involve the measurement of the first or higher diffraction orders of radiation reflected from the substrate W.

Overlay error (and other grating irregularities) is calculated from differences in intensity of reflected radiation of the "+1" and "−1" (i.e., the first) diffraction order. The actual overlay error OV is a vector in the plane of the substrate W. The substrate W can be said to define an x-y plane such that the overlay error consists of components in the x- and y-directions. Similarly, the asymmetry error (or asymmetry offset) AO is also a vector in the x-y plane. If the pattern 30 is rotated by an angle ☐ between two preliminary overlay error measurements, the first preliminary overlay error measurement $OV_o$ and the second preliminary overlay error measure ment $OV_\theta$ are related to the actual overlay error $OV$ and the asymmetry error $AO$ by the following equations:

$$OV_o = OV + AO; \text{ and}$$

$$OV_\theta = OV + \underline{R}(\theta)AO,$$

where $\underline{R}(\theta)$ is the rotation matrix $\begin{pmatrix} \cos\theta & \sin\theta \\ -\sin\theta & \cos\theta \end{pmatrix}$.

Eliminating $OV$ and separating the vectors into their x- and y-components leads to the following equations:

$$AO_x = \frac{1}{2}(OV_{0x} - OV_{\theta x}) + \frac{\sin\theta}{2(1-\cos\theta)}(OV_{0y} - OV_{\theta y}); \text{ and}$$

$$AO_y = \frac{1}{2}(OV_{0y} - OV_{\theta y}) - \frac{\sin\theta}{2(1-\cos\theta)}(OV_{0x} - OV_{\theta y}).$$

Hence, the asymmetry error $AO$ of the scatterometer can be calculated from the preliminary overlay error measurements $OV_o$ and $OV_\theta$.

The calculated asymmetry error $AO$ may be used to determine the transmission asymmetry effect by subtracting the illumination asymmetry effect from the asymmetry error.

In an alternative embodiment, the asymmetry error need not be calculated. Instead, the actual overlay error $OV$ is calculated directly from the preliminary overlay error measurements.

For example, the actual overlay error $OV$ may be calculated using the following equations:

$$OV_x = \frac{1}{2}(OV_{0x} + OV_{\theta x}) - \frac{\sin\theta}{2(1-\cos\theta)}(OV_{0y} - OV_{\theta y}); \text{ and}$$

$$OV_y = \frac{1}{2}(OV_{0y} + OV_{\theta y}) + \frac{\sin\theta}{2(1-\cos\theta)}(OV_{0x} + OV_{\theta x}).$$

Similarly, for CD measurement, the "±1" orders of the diffraction angles can be known for an "ideal" profile. The asymmetry detected using the method above can be determined for the scatterometer in question. Asymmetry in measured profiles can therefore have the scatterometer asymmetry removed from the raw data and the actual profile of the pattern on the substrate calculated. In this case, the "preliminary measurements" can be the actual diffraction spectra, because the asymmetry error correction value (i.e., the calibration value) is combined with the raw diffraction spectrum data, rather than the final CD measurement. The final CD measurement is then determined from the already-corrected diffraction spectra.

A Second Embodiment of the Present Invention

The error is specific to each scatterometer because it is dependent on features of each scatterometer such as, for example, the homogeneity of the illumination source 2 and the transmissivity of the optics in the detector 4. The calibration may be performed by determining the difference in error between the scatterometer that is to be calibrated and a reference (or "golden") scatterometer. The error in the reference apparatus may be known, in which case the error in the scatterometer to be calibrated may be determined. Alternatively, it may be assumed that the reference scatterometer has zero error. Even if the error in the reference scatterometer is not known, the apparatuses are matched to each other such that parameter measurements of a substrate W made with either scatterometer are consistent.

According to the second embodiment of the present invention, at least one measurement of the pattern 30 is made using the scatterometer that is to be calibrated. In addition, at least one measurement of the pattern 30 is made using a second scatterometer, which is used as a reference. The measurement process is the same as the first embodiment of the present invention described above. The orientation of the pattern 30 with respect to the scatterometer may be the same for both measurements made with the scatterometer to be calibrated and the reference scatterometer.

The difference in error between the two scatterometers is then calculated from a comparison of the first or higher diffraction orders of measured radiation from the measurements taken with the different scatterometers.

In order to make the calibration value less susceptible to noise, the measurement using each scatterometer may be repeated multiple times and an averaged value for each apparatus may be calculated.

In an embodiment, the pitch of the pattern 30, the polarization of illuminating radiation and the wavelength of the illuminating radiation are varied and the error difference measured again. Any one of these factors may be varied independently of the others. For example, the wavelength of radiation may be varied without varying the pitch or polarization. Once the asymmetry error difference has been determined over suitable ranges of one or more of these factors, subsequent measurements made using the scatterometer may be corrected to take into account the error difference.

An example of calculating the error difference from two measurements of a pattern 30 using different scatterometers will be explained with reference to overlay error measurements for exemplary purposes only. The above-described method of calibrating an scatterometer to account for an asymmetry error by using the scatterometer to be calibrated and a reference scatterometer to make measurements of a pattern 30 and comparing the first or higher diffraction order of measured radiation from the measurements is not restricted to overlay error measurements. The method is equally applicable to other forms of measurement that involve the measurement of the first or higher diffraction orders of radiation reflected from the substrate W, such as determining the profile (or CD) of a target pattern.

A preliminary overlay error measurement $OV_a$ made with the scatterometer to be calibrated and another preliminary overlay error measurement $OV_b$ made with a reference scatterometer are related to the actual overlay error $OV$, the asymmetry error in the scatterometer to be calibrated $AO_a$, and the asymmetry error in the reference scatterometer $AO_b$ by the following equations:

$$OV_a = OV + AO_a;$$

and $$OV_b = OV + AO_b.$$

Eliminating $OV$ from the above equations leads to the following:

$$AO_a - AO_b = OV_a - OV_b.$$

Hence, the difference asymmetry error $(AO_a - AO_b)$ between the two scatterometers is calculated. This difference may be used as a correction to overlay error measurements made using a scatterometer so that they are consistent with measurements made using the reference scatterometer.

Alternatively, the asymmetry error that is determined using the method above (namely, comparing two scatterometers) may be incorporated into the raw data, (namely, the illumination intensity as detected by the sensor) in order to give rise to an accurate intensity reading to be compared with library or model profile measurements. This gives rise to more accurate profile or CD measurements according to embodiments of the present invention.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion," respectively. The substrate referred to herein may be processed, before or after exposure, in for example a track (a tool that typically applies a layer of resist to a substrate and develops the exposed resist), a metrology tool, and/or an inspection tool. Where applicable, the disclosure herein may be applied to such and other substrate processing tools. Further, the substrate may be processed more than once, for example, in order to create a multi-layer IC, so that the term substrate used herein may also refer to a substrate that already contains multiple processed layers.

Although specific reference may have been made above to the use of embodiments of the present invention in the context of optical lithography, it will be appreciated that the invention may be used in other applications such as, for example, imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure, or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157, or 126 nm) and extreme ultra-violet (EUV) radiation (e.g., having a wavelength in the range of 5-20 nm), as well as particle beams, such as ion beams or electron beams.

The term "lens," where the context allows, may refer to any one or combination of various types of optical components, including refractive, reflective, magnetic, electromagnetic, and electrostatic optical components.

While specific embodiments of the present invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

CONCLUSION

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method comprising:
    measuring at least two measurements of a patterned target on a substrate, wherein the substrate defines an x-y plane and at least one of the at least two measurements is made using an inspection apparatus, and each measurement comprises:
        projecting a beam of radiation onto the patterned target, and
        measuring at least one diffraction order of radiation reflected from the patterned target,
        wherein the at least two measurements are made at two different rotation orientations of the patterned target;
    determining a first preliminary value of a parameter of the patterned target from the at least one of the at least two measurements;
    determining a second preliminary value of the parameter of the patterned target from the other one of the at least two measurements, wherein the first and second preliminary values comprise components in the x- and y-direction; and
    determining a residual error indicative of an error of the inspection apparatus including comparing the at least two measurements, wherein the residual error is a variation in intensity of the at least one diffraction order of radiation reflected from the patterned target caused by the error in the inspection apparatus, wherein the determining comprises using the x- and y-components from the first and second preliminary values of the parameter to calculate the residual error.

2. The method of claim 1, wherein at least two of the at least two measurements of the patterned target are made using the inspection apparatus.

3. The method of claim 2, wherein a first orientation of the patterned target with respect to the inspection apparatus for at least one of the at least two measurements is rotated by an angle D about a normal to a plane of the substrate compared to a second orientation of the patterned target for the other one of the at least two measurements.

4. The method of claim 3, wherein the angle D is at least one of 90°, 180°, and 270°.

5. The method of claim 3, wherein the at least two measurements of the patterned target are carried out at angles of 0°, 90°, 180°, or 270°.

6. The method of claim 3, wherein:
the at least two measurements each give rise to a diffraction spectrum made up of pixels representing radiation intensity for a range of angles of incidence of the diffracted light on the patterned target; and
the diffraction spectra for the at least two measurements are aligned, such that a detected intensity for each angle of incidence in a first diffraction spectrum is compared with a detected intensity for each substantially same angle of incidence in a second diffraction spectrum.

7. The method of claim 6, wherein the aligned diffraction spectra of the at least two measurements are compared, such that a difference between the at least two measurements represents a value for the residual error.

8. The method of claim 3, wherein the at least one of the at least two measurements is repeated multiple times.

9. The method of claim 1, wherein at least one of the at least two measurements is made using a reference inspection apparatus and at least another one of the at least two measurements is made using the inspection apparatus to be calibrated.

10. The method of claim 9, wherein the determining the residual error of the inspection apparatus further comprises assuming that the reference inspection apparatus has substantially no error.

11. The method of claim 9, wherein the reference inspection apparatus has a known error.

12. The method of claim 9, wherein the at least one of the at least two measurements are repeated multiple times.

13. The method of claim 9, wherein the residual error comprises a difference in error between the inspection apparatus and the reference inspection apparatus, and
wherein the determining the residual error further comprises comparing and finding a difference between the first preliminary value of the parameter measured using the inspection apparatus and a third preliminary value of the parameter measured using the reference inspection apparatus.

14. The method of claim 13, wherein the parameter is a profile of a pattern in the patterned target.

15. The method of claim 13, wherein the parameter is a critical dimension of a pattern on the patterned target.

16. The method of claim 1, wherein the determining the residual error further comprises comparing a first diffraction order of the reflected radiation in the at least two measurements.

17. The method of claim 1, wherein an illumination error is measured using a reference beam of the inspection apparatus and the illumination error is the error caused by asymmetry in components of the inspection apparatus in an optical path of the reference beam.

18. The method of claim 1, wherein the residual error is a result of an asymmetry in the inspection apparatus.

19. The method of claim 18, wherein the at least two measurements comprise measurements of asymmetry in measured diffraction spectra of the reflected radiation.

20. A method comprising:
calibrating an inspection apparatus using a method to obtain a residual error, wherein the method to obtain the residual error comprises:
measuring at least three two measurements of a patterned target on a substrate defining an x-y plane using the inspection apparatus comprising:
projecting a beam of radiation onto the patterned target; and
measuring at least one diffraction order of radiation reflected from the patterned target,
wherein the at least two measurements are two at two different rotation orientations of the patterned target,
determining a first preliminary value of a parameter of the patterned target from the at least one of the at least two measurements;
determining a second preliminary value of the parameter of the patterned target from the other one of the at least two measurements, wherein the first and second preliminary values comprise components in the x- and y-direction; and
determining a residual error indicative of an error of the inspection apparatus by comparing the at least two measurements, the residual error being a variation in intensity of at least one diffraction order of radiation reflected from the patterned target caused by the error in the inspection apparatus, wherein the determining comprises using the x- and y-components from the first and second preliminary values of the parameter to calculate the residual error;
correcting the measurement of a first or higher diffraction order based on the residual error; and
determining a parameter value of the patterned target from the corrected at least one diffraction order of radiation reflected from the patterned target.

21. The method of claim 20, wherein the parameter is a profile of a structure in the patterned target.

22. The method of claim 20, wherein the parameter is a critical dimension of a structure in the patterned target.

23. A method comprising:
measuring at least two measurements of diffraction spectra of radiation diffracted from a patterned target on a substrate defining an x-y plane using an inspection apparatus, each of the at least two measurements comprises:
projecting a beam of radiation onto the patterned target, and
measuring at least one diffraction order of radiation reflected from the patterned target, wherein the at least two measurements are made at two different rotation orientations of the patterned;
determining a first preliminary value of a parameter of the patterned target from the at least one of the at least two measurements;
determining a second preliminary value of the parameter of the patterned target from the other one of the at least two measurements wherein the first and second preliminary values comprise components in the x- and y-direction; and
determining a residual error indicative of an error of the inspection apparatus including using the x- and y-components from the first and second preliminary values of the parameter to calculate the residual error;
correcting at least one of the at least two measurements of the diffraction spectra diffracted from the patterned target based on the residual error; and
determining a critical dimension of the pattern in the patterned substrate with the corrected measurement of the diffraction spectra diffracted from the patterned target.

24. An inspection apparatus comprising:
a radiation projector configured to project radiation onto a patterned target on a substrate defining an x-y plane;

a detector configured to detect radiation reflected from the patterned target, the reflected radiation including a diffraction spectrum with at least one diffraction order;
a calibration unit configured to determine a residual error that is an error in measurement of the diffraction spectrum diffracted from the substrate caused by an error in an inspection apparatus; and
a data handling unit configured to determine a parameter based on the reflected radiation reflected from the patterned target and the residual error, wherein the data handling unit is configured to determine the residual error comprising:
measuring at least two measurements of a calibration target on the substrate, at least one of the at least two measurements is made using the inspection apparatus and each measurement comprises projecting a beam of radiation onto the calibration target and measuring at least one diffraction order of radiation reflected from the calibration target, wherein the at least two measurements are made at two different rotation orientations of the calibration target,
determining a first preliminary value of a parameter of the patterned target from the at least one of the at least two measurements,
determining a second preliminary value of the parameter of the patterned target from the other one of the at least two measurements, wherein the first and second preliminary values comprise components in the x- and y-direction, and
determining the residual error by using the x- and y-components from the first and second preliminary values of the parameter to calculate the residual error.

25. A lithographic apparatus comprising:
an illumination source configured to condition a radiation beam;
a support constructed to support a patterning device, the patterning device being capable of imparting the radiation beam with a pattern in its cross-section to form a patterned radiation beam;
a substrate table constructed to hold a substrate defining an x-y plane;
a projection system configured to project the patterned radiation beam onto a target portion of the substrate; and
an inspection apparatus configured to measure a parameter of the substrate, the inspection apparatus comprising:
a radiation projector configured to project a radiation onto a patterned target on the substrate,
a detector configured to detect the radiation reflected from the patterned target, wherein the reflected radiation includes a diffraction spectrum with at least one diffraction order,
a calibration unit configured to determine a residual error, wherein the residual error is an error in measurement of the diffraction spectrum diffracted from the substrate caused by an error in the inspection apparatus, and
a data handling unit configured to determine the parameter based on the reflected radiation reflected from the patterned target and the residual error, wherein determining of the residual error comprises:
measuring at least three two measurements of a calibration target on the substrate, wherein at least one of the at least three two measurements is made using the inspection apparatus and each measurement comprises:
projecting a beam of radiation onto the calibration target, and
measuring at least one diffraction order of radiation reflected from the calibration target, wherein the at least two measurements are made at two different rotation orientations of the calibration target,
determining a first preliminary value of a parameter of the patterned target from the at least one of the at least two measurements,
determining a second preliminary value of the parameter of the patterned target from the other one of the at least two measurements, wherein the first and second preliminary values comprise components in the x- and y-direction, and
determining the residual error by using the x- and y-components from the first and second preliminary values of the parameter to calculate the residual error.

26. A lithographic cell comprising:
a coater configured to coat substrates with a radiation sensitive layer;
a lithographic apparatus configured to expose images onto the radiation sensitive layer of substrates coated by the coater;
a developer configured to develop images exposed by the lithographic apparatus; and
an inspection apparatus configured to measure a parameter of a substrate defining an x-y plane, the inspection apparatus comprising:
a radiation projector configured to project a radiation onto a patterned target on the substrate;
a detector configured to detect the radiation reflected from the patterned target, wherein the reflected radiation includes a diffraction spectrum with at least one diffraction order;
a calibration unit configured to determine a residual error, wherein the residual error is an error in measurement of the diffraction spectrum diffracted from the substrate caused by an error in the inspection apparatus; and
a data handling unit configured to determine the parameter based on the reflected radiation reflected from the patterned target and the residual error, wherein determining of the residual error comprises:
measuring at least two measurements of a calibration target on the substrate, wherein at least one of the at least two measurements is made using the inspection apparatus and each measurement comprises:
projecting a beam of radiation onto the calibration target; and
measuring at least one diffraction order of radiation reflected from the calibration target, wherein the at least two measurements are made at two different rotation orientations of the calibration target;
determining a first preliminary value of a parameter of the patterned target from the at least one of the at least two measurements;
determining a second preliminary value of the parameter of the patterned target from the other one of the at least two measurements, wherein the first and second preliminary values comprise components in the x- and y-direction; and
determining the residual error by using the x- and y-components from the first and second preliminary values of the parameter to calculate the residual error.

* * * * *

UNITED STATES PATENT AND TRADEMARK OFFICE
CERTIFICATE OF CORRECTION

PATENT NO.      : 9,188,875 B2
APPLICATION NO. : 13/132011
DATED           : November 17, 2015
INVENTOR(S)     : Cramer et al.

It is certified that error appears in the above-identified patent and that said Letters Patent is hereby corrected as shown below:

IN THE CLAIMS
In column 24, line 1, claim 20, after "at least", please delete "three".
In column 24, line 52, claim 23, after "measurements", please insert --,--.
In column 25, line 61, claim 25, after "at least", please delete "three".
In column 25, line 63, claim 25, after "at least", please delete "three".

Signed and Sealed this
Twenty-ninth Day of March, 2016

Michelle K. Lee
*Director of the United States Patent and Trademark Office*